United States Patent [19]

Laurent et al.

[11] 4,289,763
[45] Sep. 15, 1981

[54] NOVEL CORTICOIDS, THE PREPARATION THEREOF AND THE USE THEREOF

[75] Inventors: Henry Laurent; Rudolf Wiechert; Hans Wendt; Joachim-Friedrich Kapp, all of Berlin, Fed. Rep. of Germany

[73] Assignee: Schering Aktiengesellschaft, Berlin and Bergkamen, Fed. Rep. of Germany

[21] Appl. No.: 150,826

[22] Filed: May 19, 1980

[30] Foreign Application Priority Data

May 18, 1979 [DE] Fed. Rep. of Germany ....... 2920726

[51] Int. Cl.³ .............................................. C07J 5/00
[52] U.S. Cl. ................................ 424/243; 260/397.45
[58] Field of Search .................... 260/397.45; 424/243

[56] References Cited
U.S. PATENT DOCUMENTS 3,956,347  5/1976  Laurent et al. .................. 260/397.1

Primary Examiner—Elbert L. Roberts
Attorney, Agent, or Firm—Millen & White

[57] ABSTRACT

Corticoids of the formula

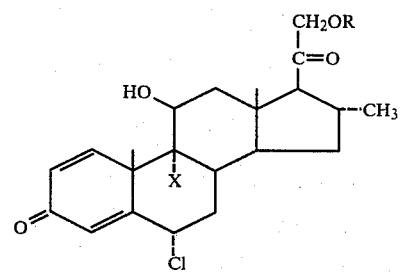

wherein
 X is fluorine, chlorine and
 R is hydrogen, $C_{1-6}$ alkanoyl, benzoyl or —OCO—A—COOH
wherein
 A is a carbon-to-carbon bond or a $C_{1-6}$ hydrocarbon chain,
or when
 R is —OCO—A—COOH, the physiologically acceptable salts thereof with a base,
have high effectiveness, e.g., antiinflammatorily but with attendant low side effects.

13 Claims, No Drawings

NOVEL CORTICOIDS, THE PREPARATION THEREOF AND THE USE THEREOF

BACKGROUND OF THE INVENTION

The present invention concerns new corticoids showing pharmacological activity.

As is well-known, corticoid-containing pharmaceutical preparations are of superior significance nowadays, due tp their antiinflammatory activity. They are, accordingly, useful for therapy in, for example, internal medicine, dermatology, etc. and also in all other clinical-medical areas. They are frequently instrumental in saving the patient's life.

However, since all systemically effective corticoids cause strong side effects (e.g., changes in the blood pattern, destruction of the lymphatic system, increase in susceptibility to infections, effect on sodium retention, atrophies of the spleen, the thymus, the adrenal gland, the body weight, etc.), therapy with corticoid-containing preparations is problematic. This is especially true since these side effects are constantly present in long-term therapy with corticoids, are often externally recognizable by the so-called Cushing syndrome of the patient and are not infrequently life-threatening.

SUMMARY OF THE INVENTION

Accordingly, it is an object of this invention to provide novel corticoids having high effectiveness, e.g., antiinflammatorily, but with attendant low side effects.

Upon further study of the specification and appended claims, further objects and advantages of this invention will become apparent to those skilled in the art.

These objects have been achieved in one aspect by providing new corticoids of Formula I

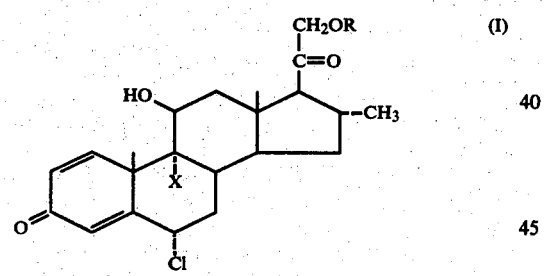

wherein
X is fluorine or chlorine and
R is hydrogen or an acyl residue of 1–8 carbon atoms.

DETAILED DISCUSSION

In Formula I, the substituent R is hydrogen or acyl of 1–8 carbon atoms.

The acyl residues R preferably are formyl, $C_{1-8}$ alkanoyl or benzoyl. Suitable alkanoyl residues include, for example, acetyl, propionyl, butyryl, isobutyryl, pentanoyl, trimethylacetyl and hexanoyl.

On the other hand, the acyl residues R can also preferably be

wherein
A is a carbon-to-carbon bond or a hydrocarbon chain of 1–6 carbon atoms and
Y is hydrogen or the cation of a physiologically acceptable base, i.e., the physiologically acceptable salts of the COOH group of such steroids are included. Suitable hydrocarbon moieties A include branched or straight-chain-$C_{1-6}$ alkylene and —$C_{2-6}$ alkenylene groups such as methylene, dimethylene, trimethylene, tetramethylene, ethylidene, 2,2-propylidene or vinylene groups.

These latter water-soluble corticoids of formula I are, thus, 21-monoesters of aliphatic dicarboxylic acids, e.g., of oxalic acid, malonic acid, succinic acid, glutaric acid, adipic acid, pimelic acid, maleic acid, fumaric acid, etc., and the salts thereof with physiologically acceptable bases, such as alkali or alkaline earth metal salts (e.g., sodium salts, potassium salts, or calcium salts), ammonium salts, copper (II) salts, methylglucamine salts and amino acid salts, as are conventional.

The novel corticoids of Formula I can be prepared in accordance with processes well-known to those skilled in the art (U.S. Pat. No. 3,828,083, whose disclosure is incorporated by reference herein), e.g., as follows, by (a) opening the epoxide ring of a steroid of Formula II

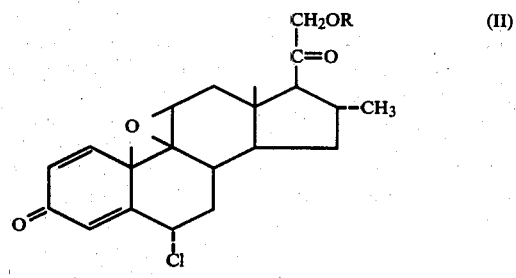

wherein
R is as defined for Formula I, with hydrogen chloride or hydrogen fluoride; or (b) chemically adding hydrogen chloride to the 9,11-double bond of a steroid of Formula III

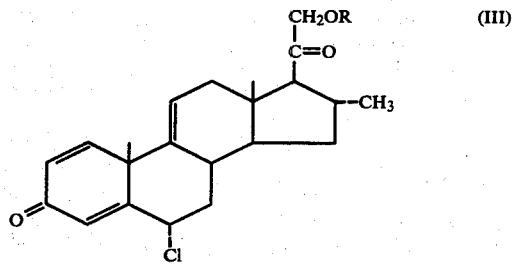

wherein
R is as defined for Formula I, and/or saponifying any ester groups which are present and/or esterifying any 21-hydroxy groups which are present, using in each instance fully conventional methods.

Any necessary saponifications and/or esterifications can be carried out using fully conventional methods, e.g., as disclosed in U.S. Pat. No. 3,232,839. whose disclosure is incorporated by reference herein.

The starting compounds of Formulae II and III used in the process of this invention can be produced in simple analogy to the process set forth below from 6α-chloro-11β,21-dihydroxy-16α-methyl-1,4-pregnadiene-3,20-dione, a compound which, according to the known state of the art (see, e.g., U.S. Pat. No. 3,232,839) can be prepared only with difficulty.

However, by following the procedure described hereinbelow, this compound is accessible in a very simple way. As a result, the corticoids of this invention can be prepared at relatively low cost compared to other highly efficacious corticoids. This is important in view of the high costs of the active agents conventional in corticoid-containing medicine specialties.

Pharmaceutical preparations containing corticoids of this invention (e.g., one or two of them) show in pharmacological tests a strong antiinflammatory activity and are distinguished by a very favorable dissociation between desirable inflammation-inhibitory effectiveness and undesired side effects. The novel corticoids of this invention can be processed into medical specialty preparations in fully conventional fashion, by converting them, optionally with suitable additives, carriers, solubilizers, stabilizers, and flavor-ameliorating agents, into the desired forms of administration, such as ointments, creams, tablets, dragees, capsules, solution, etc.

Accordingly, the pharmacologically active compounds of this invention can be processed in accordance with conventional methods of galenic pharmacy to produce medicinal agents for administration to patients, e.g., mammals, including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Ointments or creams preferably contain 0.05% to 1% of the active agent; tablets, dragees, or capsules contain preferably 5–200 mg of the active agent.

It is furthermore possible to utilize pulverulent mixtures as inhalants, containing, for example, 0.5–20 mg of active agent in addition to a water-soluble vehicle, such as lactose.

For treatment purposes, preferably 1–1000 mg of the active agent is administered to patients per day (or 0,02–20 mg/kg/day), depending on the graveness of the condition of the disease, in analogy with the administration of the conventional antiinflammatory agent difluocortolone.

The thus-obtained drug specialties can be used in the treatment of those diseases wherein, customarily, therapy with corticoids is indicated. These include, for example: allergic reactions, acute shock and collapse, status asthmaticus [asthmatic shock], cerebral edema, extensive burns, grave metabolic disturbances, acute grave dermatoses, Quincke's edema, acute infectious diseases (supplementary therapy), polyarthritis rheumatica, acute and chronic connective tissue diseases, allergic, rheumatological and dermatological diseases responding to oral corticoid therapy, coticoid-sensitive inflammations of the oral mucosa, allergic reactions, lichen, inflammatory and allergic diseases of the eye, iritis, iridocyclitis, conjunctivitis, diseases of the frontal uvea, allergic and chronic rhinitides, rhinitis vasomotorica, non-purulent sinusitis, hay fever, and colitis ulcerosa.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation of
6α-chloro-11β,21-dihydroxy-16α-methyl-1,4-pregnadiene-3,20-dione (a) A solution of 110 g of 21-acetoxy-16α-methyl-4-pregnene-3,20-dione in 550 ml of ethanol and 550 ml of 1,2-dimethoxyethane is combined with 11.2 g of p-toluenesulfonic acid and 16 g of triethyl orthoformate. The reaction mixture is heated for 50 minutes to 40° C., then cooled to 10° C., combined with 12 ml of pyridine as well as 3 g of sodium acetate, and poured into 3 l. of ice water. The reaction product is extracted with dichloromethane, the extract is washed with water, dried over sodium sulfate, and evaporated under vacuum. The residue is dissolved in 800 ml of acetone, and the solution is combined with 540 ml of water, 17 ml of pyridine, and 94 g of sodium acetate. Under agitation, 106 g of N-chlorosuccinimide is added thereto and the mixture stirred for 30 minutes at 5° C. Then a solution of 37 g of sodium bisulfite in 145 ml of water is added thereto, and the mixture is agitated for another 30 minutes. The reaction solution is stirred into 15 l. of ice water, the thus-precipitated product is filtered off, washed with water, and dried in the open air. The crude product of 122 g is chromatographed on silica gel. The desired product is eluted with 10–22% acetone-dichloromethane and recrystallized from acetone-dichloromethane. Yield: 62.8 g of 21-acetoxy-6α-chloro-11β-hydroxy-16α-methyl-4-pregnene-3,20-dione, m.p. 209° C. $[\alpha]_D^{25} = +176°$ (pyridine). UV: $\epsilon_{237} = 14,100$ (methanol).

(b) 2.0 g of 21-acetoxy-6α-chloro-11β-hydroxy-16α-methyl-4-pregnene-3,20-dione is dissolved in 100 ml of dioxane; 3 g of 2,3-dichloro-5,6-dicyano-1,4-benzoquinone is added thereto and the mixture heated for 24 hours to boiling. After cooling, the mixture is vacuum-filtered from the undissolved matter, washed with dichloromethane, and concentrated under vacuum. The crude product is chromatographed on silica gel. With 37–46% acetone-hexane, after recrystallization from acetone-diisopropyl ether, 1.08 g of 21-acetoxy-6α-chloro-11β-hydroxy-16α-methyl-1,4-pregnadiene-3,20-dione is obtained, m.p. 208.5° C. $[\alpha]_D^{25} = +90°$ (chloroform). UV: $\epsilon_{243} = 15,700$ (methanol).

(c) 1.5 g of 21-acetoxy-6α-chloro-11β-hydroxy-16α-methyl-1,4-pregnadiene-3,20-dione is dissolved in 42 ml of methanol; 1.3 ml of 70% perchloric acid is added thereto and the mixture allowed to stand at room temperature for 20 minutes. The reaction mixture is stirred into ice water, the thus-obtained precipitate is filtered off, washed with water, and dried in the open air. After recrystallization from acetone-diisopropyl ether, 1.02 g of 6α-chloro-11β,21-dihydroxy-16α-methyl-1,4-pregnadiene-3,20-dione is obtained, m.p. 128° C. $[\alpha]_D^{25} = +55°$ (chloroform). UV: $\epsilon_{242} = 14,600$ (methanol).

EXAMPLE 1

(a) A solution of 14.0 g of 21-acetoxy-6α-chloro-11β-hydroxy-16α-methyl-1,4-pregnadiene-3,20-dione in 29 ml of collidine and 90 ml of DMF is combined with 11 ml of methanesulfonic acid chloride containing 3% sulfur dioxide and agitated at room temperature. After 15 minutes, 15 ml of water is added under ice cooling. The thus-obtained precipitate is filtered off, washed with water, and dried in the open air. The crude product is chromatographed on silica gel. With 33–61% ethyl acetate-hexane, 12.1 g of 21-acetoxy-6α-chloro-16α-methyl-1,4,9(11)-pregnatriene-3,20-dione is obtained. A sample, recrystallized from ethyl acetate-hexane, melts at 181° C. $[\alpha]_D^{25} = +22°$ (chloroform).

UV: $\epsilon_{236} = 15,600$ (methanol).

(b) A solution of 12.0 g of 21-acetoxy-6α-chloro-16α-methyl-1,4,9(11)-pregnatriene-3,20-dione in 120 ml of dioxane is stirred at room temperature after adding 11.1 g of N-bromosuccinimide and 60 ml of 10% perchloric acid and, after 60 minutes, poured into ice water. The thus-precipitated product is filtered off, washed with water, dried in the air, and dissovled in 215 ml of ethanol. After adding 29 g of potassium acetate, the solution is heated for 8 hours to 60° C. under argon. Then the mixture is concentrated to a volume of 60 ml under vacuum, and stirred into ice water. The precipitated product is isolated and chromatographed on silica gel. With 8–9% acetone-hexane, after recrystallization from acetone-diisopropyl ether, 5.2 g of 21-acetoxy-6α-chloro-9,11β-epoxy-16α-methyl-9β-pregna-1,4-diene-3,20-dione is obtained, m.p. 189° C. $[\alpha]_D^{25} = +57°$ (chloroform).

UV: $\epsilon_{247} = 15,600$ (methanol).

(c) 800 mg of 21-acetoxy-6α-chloro-9,11β-epoxy-16α-methyl-9β-pregna-1,4-diene-3,20-dione in 3 ml of pyridine is added to 11 ml of a solution, cooled to −60° C., of hydrogen fluoride in pyridine (70% strength). The mixture is allowed to stand for 15 hours at room temperature and stirred into 50 ml of 10% ammonium hydroxide solution. The mixture is extracted with methylene chloride, washed with dilute hydrochloric acid as well as with water, dried and concentrated under vacuum. The residue is chromatographed on silica gel. With 33–44% ethyl acetate-hexane, 710 mg is obtained which is recrystallized from ethyl acetate-hexane. Yield: 600 mg of 21-acetoxy-6α-chloro-9-fluoro-11β-hydroxy-16α-methyl-1,4-pregnadiene-3,20-dione, m.p. 240° C. $[\alpha]_D^{25} = +82°$ (chloroform).

UV: $\epsilon_{239} = 15,700$ (methanol).

EXAMPLE 2

A solution of 9.0 g of 21-acetoxy-6α-chloro-16α-methyl-1,4,9(11)-pregnatriene-3,20-dione in 340 ml of dioxane is combined with 80 ml of water, 27 g of N-chlorosuccinimide, and 27 ml of 70% perchloric acid. The mixture is allowed to react for 30 minutes at room temperature and poured into ice water. The thus-obtained precipitate is filtered off, washed with water, dried in the air, and chromatographed on silica gel. With 35–53% ethyl acetate-hexane, 7.23 g is obtained which, recrystallized from ethyl acetate, yields 5.33 g of 21-acetoxy-6α,9-dichloro-11β-hydroxy-16α-methyl-1,4-pregnadiene-3,20-dione, m.p. 238° C. $[\alpha]_D^{25} = +110°$ (chloroform).

UV: $\epsilon_{239} = 13,300$ (methanol).

EXAMPLE 3

1.90 g of 21-acetoxy-6α,9-dichloro-11β-hydroxy-16α-methyl-1,4-pregnadiene-3,20-dione is dissolved in 53 ml of methanol. The mixture is conbined with 1.7 ml of 70% perchloric acid and allowed to stand for 20 hours at room temperature. The reaction mixture is poured into ice water; the precipitated product is isolated and chromatographed on silica gel. With 37–52% ethyl acetate-dichloromethane, after recrystallization from acetone-diisopropyl ether, 807 mg of 6α,9-dichloro-11β,21-dihydroxy-16α-methyl-1,4-pregnadiene-3,20-dione is obtained, m.p. 230° C. $[\alpha]_D^{25} = +99°$ (chloroform).

UV: $\epsilon_{238} = 15,000$ (methanol).

EXAMPLE 4

A solution of 250 mg of 6α,9-dichloro-11β,21-dihydroxy-16α-methyl-1,4-pregnadiene-3,20-dione in 5 ml of pyridine and 2.5 ml of butyric anhydride is stirred for 15 hours at room temperature. The mixture is combined with ice water and the thus-formed precipitate is filtered off after another 3 hours. The moist crude product is taken up in dichloromethane; the solution is washed with water, dried over sodium sulfate, and evaporated under vacuum. The residue is recrystallized from acetone-diisopropyl ether. Yield: 166 mg of 21-butyryloxy-6α,9-dichloro-11β-hydroxy-16α-methyl-1,4-pregnadiene-3,20-dione, m.p. 225° C. $[\alpha]_D^{25} = +111°$ (chloroform).

UV: $\epsilon_{238} = 15,500$ (methanol).

EXAMPLE 5

A solution of 250 mg of 6α,9-dichloro-11β,21-dihydroxy-16α-methyl-1,4-pregnadiene-3,20-dione in 5 ml of pyridine is stirred, after adding 2.5 ml of valeric anhydride, for 15 hours at room temperature. The working-up procedure set forth in Example 4 is followed. After recrystallization from acetone-diisopropyl ether, 165 mg of 6α,9-dichloro-11β-hydroxy-16α-methyl-21-valeryloxy-1,4-pregnadiene-3,20-dione is obtained, m.p. 218° C. $[\alpha]_D^{25} = +113°$ (chloroform).

UV: $\epsilon_{238} = 15,500$ (methanol).

EXAMPLE 6

A solution of 1.0 g of 6α,9-dichloro-11β,21-dihydroxy-16α-methyl-1,4-pregnadiene-3,20-dione in 10 ml of 1,2-dichloroethane is combined with 2.5 ml of pivalic anhydride, 1.0 g of sodium hydroxide, as well as 5 ml of water and stirred for 90 minutes at 30° C. After adding 50 ml of dichloromethane the organic phase is separated, washed with water, dried over sodium sulfate, and concentrated under vacuum. The residue is chromatographed on silica gel. With 19–26% ethyl acetate-dichloromethane, after recrystallization from acetone-diisopropyl ether, 245 mg of 6α,9-dichloro-11β-hydroxy-16α-methyl-21-trimethylacetoxy-1,4-pregnadiene-3,20-dione is obtained, m.p. 238° C. $[\alpha]_D^{25} = +110°$ (chloroform).

UV: $\epsilon_{238} = 15,500$ (methanol).

EXAMPLE 7

(a) 2.5 g of 6α-chloro-11β,21-dihydroxy-16α-methyl-1,4-pregnadiene-3,20-dione is stirred in 50 ml of pyridine and 25 ml of butyric anhydride at room temperature. After 15 hours the mixture is poured into ice water, the thus-produced precipitate is filtered off after allowing the mixture to stand for 3 hours, then washed with water, and dissolved in dichloromethane. After drying and concentration of the solution the remaining residue is recrystallized from acetone-diisopropyl ether. Yield: 2.65 g of 21-butyryloxy-6α-chloro-11β-hydroxy-16α-methyl-1,4-pregnadiene-3,20-dione, m.p. 192° C. $[\alpha]_D^{25} = +82°$ (chloroform).

UV: $\epsilon_{234} = 15,000$ (methanol).

(b) 2.4 g of 21-butyryloxy-6α-chloro-11β-hydroxy-16α-methyl-1,4-pregnadiene-3,20-dione is converted, as described in Example 1(a), into 21-butyryloxy-6α-chloro-16α-methyl-1,4,9(11)-pregnatriene-3,20-dione.

Yield: 2.1 g.

(c) 2.1 g of 21-butyryloxy-6α-chloro-16α-methyl-1,4,9(11)-pregnatriene-3,20-dione is converted into 21-butyryloxy-6α,9-dichloro-11β-hydroxy-16αmethyl-1,4-pregnadiene-3,20-dione under the conditions indicated in Example 2.

Yield: 1.23 g, m.p. 223° C.

EXAMPLE 8

(a) A solution of 2.25 g of 6α-chloro-11β,21-dihydroxy-16α-methyl-1,4-pregnadiene-3,20-dione in 50 ml of pyridine and 25 ml of valeric anhydride is stirred for 15 hours at room temperature and thereafter poured into ice water. After 4 hours the thus-formed precipitate is filtered off, washed with water, and dissolved in dichloromethane. The solution is dried over sodium sulfate and evaporated under vacuum. The residue is recrystallized from acetone-diisopropyl ether. Yield: 2.11 g of 6α-chloro-11β-hydroxy-16α-methyl-21-valeryloxy-1,4-pregnadiene-3,20-dione, m.p. 229.5° C. $[\alpha]_D^{25} = +83°$ (chloroform).

UV: $\epsilon_{243} = 15,600$ (methanol).

(b) 2.0 g of 6α-chloro-11β-hydroxy-16α-methyl-21-valeryloxy-1,4-pregnadiene-3,20-dione is converted, as described in Example 1(a), into 6α-chloro-16α-methyl-21-valeryloxy-1,4,9(11)-pregnatriene-3,20-dione. Yield: 1.74 g.

(c) 1.74 g of 6α-chloro-16α-methyl-21-valeryloxy-1,4,9(11)-pregnatriene-3,20-dione is converted, under the conditions indicated in Example 2, into 6α,9-dichloro-11β-hydroxy-16α-methyl-21-valeryloxy-1,4-pregnadiene-3,20-dione. Yield: 1.02 g, m.p. 219° C.

EXAMPLE 9

(a) A solution of 2.0 g of 6α-chloro-11β,21-dihydroxy-16α-methyl-1,4-pregnadiene-3,20-dione in 20 ml of 1,2-dichloroethane is combined with 5.2 ml of pivalic anhydride as well as 2.0 g of sodium hydroxide in 12 ml of water and vigorously agitated for 90 minutes. Then the mixture is diluted with dichloromethane, the organic phase is separated, washed with water, dried over sodium sulfate, and concentrated under vacuum. The residue is chromatographed on silica gel; with 50% ethyl acetate-hexane, after recrystallization from acetone-diisopropyl ether, 672 mg of 6α-chloro-11β-hydroxy-16α-methyl-21-trimethylacetoxy-1,4-pregnadiene-3,20-dione is obtained, m.p. 189° C. $[\alpha]_D^{25} = +78°$ (chloroform).

UV: $\epsilon_{243} = 15,400$ (methanol).

(b) 600 mg of 6α-chloro-11β-hydroxy-16α-methyl-21-trimethylacetoxy-1,4-pregnadiene-3,20-dione is converted, as described in Example 1(a), into 6α-chloro-16α-methyl-21-trimethylacetoxy-1,4,9(11)-pregnatriene-3,20-dione.

Yield: 402 mg.

(c) 402 mg of 6α-chloro-16α-methyl-21-trimethylacetoxy-1,4,9(11)-pregnatriene-3,20-dione is converted, under the conditions set forth in Example 2, into 6α,9-dichloro-11β-hydroxy-16α-methyl-21-trimethylacetoxy-1,4-pregnadiene-3,20-dione.

Yield: 233 mg, m.p. 234° C.

EXAMPLE 10

(a) 2.3 g of 6α-chloro-11β,21-dihydroxy-16α-methyl-1,4-pregnadiene-3,20-dione is dissolved in a mixture of 55 ml of pyridine and 27 ml of caproic anhydride, and the mixture is stirred for 20 hours at room temperature. The reaction mixture is combined with 10 ml of water, heated on a steam bath for 3 hours, and stirred into ice water. The thus-obtained precipitate is filtered off and dissolved in dichloromethane. The solution is washed with water, dried over sodium sulfate, and evaporated under vacuum. The residue is recrystallized from methanol. Yield: 2.0 g of 6α-chloro-21-hexanoyloxy-11β-hydroxy-16α-methyl-1,4-pregnadiene-3,20-dione, m.p. 247° C. $[\alpha]_D^{25} = +118$ (pyridine).

UV: $\epsilon_{242} = 13,400$ (methanol).

(b) 1.9 g of 6α-chloro-21-hexanoyloxy-11β-hydroxy-16α-methyl-1,4-pregnadiene-3,20-dione is converted, under the conditions indicated in Example 1, into 6α-chloro-9-fluoro-21-hexanoyloxy-11β-hydroxy-16α-methyl-1,4-pregnadiene-3,20-dione.

Yield: 494 mg, m.p. 268° C. $[\alpha]_D^{25} = +78°$ (chloroform).

UV: $\epsilon_{239} = 15,600$ (methanol).

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A corticoid of the formula

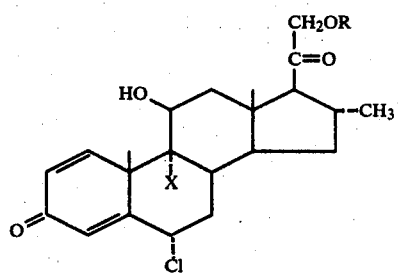

wherein

X is fluorine or chlorine and

R is hydrogen, $C_{1-6}$ alkanoyl, benzoyl or —OCO—A—COOH wherein

A is a carbon-to-carbon bond or a $C_{1-6}$ hydrocarbon chain, or when

R is —OCO—A—COOH, the physiologically acceptable salts thereof with a base.

2. 21-Acetoxy-6α-chloro-9α-fluoro-11β-hydroxy-16α-methyl-1,4-pregnadiene-3,20-dione, a compound of claim 1.

3. 21-Acetoxy-6α,9α-dichloro-11β-hydroxy-16α-methyl-1,4-pregnadiene-3,20-dione, a compound of claim 1.

4. 6α,9α-Dichloro-11β,21-dihydroxy-16α-methyl-1,4-pregnadiene-3,20-dione, a compound of claim 1.

5. 21-Butyryloxy-6α,9α-dichloro-11β-hydroxy-16α-methyl-1,4-pregnadiene-3,20-dione, a compound of claim 1.

6. 6α,9α-Dichloro-11β-hydroxy-16α-methyl-21-valeryloxy-1,4-pregnadiene-3,20-dione, a compound of claim 1.

7. 6α,9α-Dichloro-11β-hydroxy-16α-methyl-21-trimethylacetoxy-1,4-pregnadiene-3,20-dione, a compound of claim 1.

8. 6α-Chloro-9α-fluoro-21-hexanoyloxy-11β-hydroxy-16α-methyl-1,4-pregnadiene-3,20-dione, a compound of claim 1.

9. A pharmaceutical composition comprising a corticoidally effective amount of a compound of claim 1 and a pharmaceutically acceptable carrier.

10. The pharmaceutical composition of claim 9 comprising two such corticoidally effective compounds.

11. A method of achieving corticoidal effects in a patient in need of such treatment comprising administering to the patient a corticoidally effective amount of a compound of claim 1.

12. A compound of claim 1 wherein R is $C_{1-6}$ alkanoyl or benzoyl.

13. A compound of claim 1 wherein R is —OCO—A—COOH.

* * * * *